(12) United States Patent
Fushihara et al.

(10) Patent No.: US 6,383,127 B2
(45) Date of Patent: May 7, 2002

(54) METHOD OF CRYSTALLIZING TETRABROMOBISPHENOL A

(75) Inventors: Hiroshi Fushihara; Hidemasa Suetsugu; Takahiro Matsunaga, all of Yamaguchi (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 09/854,535

(22) Filed: May 15, 2001

(30) Foreign Application Priority Data

May 16, 2000 (JP) .......................................... P12-148612

(51) Int. Cl.⁷ .............................................. C07C 37/84
(52) U.S. Cl. ...................................................... 567/725
(58) Field of Search .................................. 568/725, 726

(56) References Cited

U.S. PATENT DOCUMENTS 5,302,761 A * 4/1994 Tamabayasi
5,446,212 A * 8/1995 Sanders \* cited by examiner

*Primary Examiner*—Michael L. Shippen
(74) *Attorney, Agent, or Firm*—Piper Marbury Rudnick & Wolfe LLP; Steven B. Kelber

(57) ABSTRACT

A method of crystallizing tetrabromobisphenol A is described, which comprises continuously and simultaneously feeding a methanolic tetrabromobisphenol A solution and water separately to a first crystallizer to obtain a slurry in which a part of the tetrabromobisphenol A is crystallized and continuously and simultaneously feeding said slurry and water separately to a second crystallizer to crystallize substantially the whole amount of the tetrabromophisphenol A.

19 Claims, No Drawings

METHOD OF CRYSTALLIZING TETRABROMOBISPHENOL A

FIELD OF THE INVENTION

This invention relates to a method of crystallizing tetrabromobisphenol A (hereinafter TBA) widely used as a flame retardant for synthetic resins. More particularly, it relates to a method for effectively and efficiently obtaining TBA crystals of high quality in a continuous manner from a methanol solution of TBA.

BACKGROUND OF THE INVENTION

TBA is generally produced by brominating bisphenol A (hereinafter BPA) with bromine in an organic solvent, such as a lower alkyl alcohol or a halogenated hydrocarbon. In industrial scale production, methanol is chosen as a solvent for ease of handling and relatively suppressed formation of impurities. Bromine is used in a slight excess over a theoretical amount. TBA in the methanolic reaction solution is commonly recovered as crystals by addition of a poor solvent, such as water.

JP-B-41-3376 (The term "JP-B" as used herein means an "examined Japanese patent publication") discloses a process of producing TBA crystals comprising allowing bromine in excess over a theoretical amount to react BPA in methanol as a preferred alcohol, raising the temperature of the reaction mixture, allowing by-produced hydrogen bromide and residual bromine to react with methanol to produce methyl bromide, which is recovered by distillation, and then adding water to the methanolic TBA solution to crystallize TBA in a batch system.

JP-B-53-20494 proposes a similar technique, in which the reaction mixture obtained by bromination of a methanol solution of BPA is heated, and evolved hydrogen bromide and residual bromine are recovered as methyl bromide. In this process, the inventors use sulfuric acid as a poor solvent for batchwise crystallization of TBA in a methanol solution, asserting that TBA crystals obtained by addition of sulfuric acid are less colored than those obtained by addition of water.

JP-A-2-270833 (The term "JP-A" as used herein means an "unexamined published Japanese patent application") teaches a process comprising heating the reaction mixture obtained by bromination of BPA in methanol to recover residual bromine as methyl bromide, reducing unrecovered residual bromine with sodium sulfite, and then crystallizing TBA in a usual manner, such as addition of water.

In these related arts the excess bromine is allowed to react with methanol, a solvent, to produce methyl bromide, which is recovered. Although methyl bromide was formerly a useful by-product finding use as a fumigant, etc., it has recently been accused of causing destruction of the ozonosphere. Therefore, co-production of methyl bromide is now to be avoided. Additionally the related arts adopt, in common, a batch system for crystallizing TBA by addition of water or sulfuric acid, achieving low production efficiency and insufficient crystal quality.

There have been proposed processes of producing TBA without co-producing methyl bromide. For example, JP-A-2-196747 discloses a process in which the residual bromine of the reaction mixture obtained by brominating BPA in methanol is reduced to hydrogen bromide with an aqueous hydrazine solution, and water is then added to crystallize TBA in a batch system. Involving no production of methyl bromide, this process can be seen as environment friendly. The residual bromide can completely be reduced to hydrogen bromide with hydrazine. However, conducted in a batch system, the TBA crystallization by addition of water is unsatisfactory in production efficiency and quality.

JP-A-3-246245 proposes a process comprising reducing the bromination reaction mixture of BPA with an aqueous hydrazine solution and batchwise crystallizing TBA in methanol by addition of water at a temperature of −15 to 15° C. to obtain TBA crystals reduced in both hydrolyzable bromine content and inorganic bromide ion content. The process, being a batch system, too, has low production efficiency. In addition, because the crystallization is at low temperature, the resulting crystals are small only to need an increased load in filtration and washing.

JP-A-4-9346, which is basically the same as JP-A-3-246245, teaches that TBA crystals reduced in contents of hydrolyzable bromine and inorganic bromide ion which are impurities can be obtained by limiting the amount of water and the rate of dropping addition of water in crystallization to 30 to 100% by weight and 5 to 40% by weight per hour, respectively, based on the reaction solvent. This process possesses the drawback of having a low recovery as well as low production efficiency due to the batch system.

All these conventional processes of recovering TBA crystals without co-producing methyl bromide adopt a batch system for crystallizing TBA by addition of water or sulfuric acid to a methanol solution of TBA. The low production efficiency of batchwise crystallization and the accompanying process and operation complexity have made the processes still unsatisfactory for industrial scale production. Further, the quality of TBA crystals obtained are not satisfactory. It has therefore been keenly demanded to develop an effective and efficient method for recovering high-quality TBA crystals from a methanolic TBA solution by using water which is easier to handle than sulfuric acid as a poor solvent.

SUMMARY OF THE INVENTION

An object of the present invention is to provide a method for effectively and efficiently obtaining TBA crystals of high quality in a continuous manner from a methanol solution of TBA.

As a result of investigation, the present inventors have surprisingly found that the problems associated with conventional techniques of TBA crystallization from a methanol solution by addition of water can be solved by a method in which crystallization by addition of water is carried out continuously but in two divided stages.

They have additionally found that high quality TBA crystals can be obtained with satisfactory crystal growth by continuously and simultaneously feeding a bromine-containing methanolic TBA solution, a reducing agent and water separately into a crystallizer without being accompanied by incorporation of bromine into the TBA crystals. This is a totally unexpected finding, considered from the state-of-the-art belief that it is impossible to crystallize TBA directly from a bromine-containing methanol solution of TBA. The present invention has been completed based on these findings.

The present invention provides:
(1) A method of crystallizing TBA which comprises continuously and simultaneously feeding a methanolic TBA solution and water separately to a first crystallizer to obtain a slurry in which a part of the TBA is crystallized and continuously and simultaneously feeding the slurry and water separately to a second crystallizer to crystallize substantially the whole amount of the TBA (first aspect);

(2) A method of crystallizing TBA which comprises continuously and simultaneously feeding a methanolic TBA solution containing bromine, a reducing agent, and water separately to a crystallizer to cause the TBA to crystallize and to cause bromine to be reduced simultaneously (second aspect); and (3) A method of crystallizing TBA which comprises continuously and simultaneously feeding a methanolic TBA solution containing bromine, a reducing agent, and water separately to a first crystallizer to obtain a slurry in which a part of the TBA is crystallized and continuously and simultaneously feeding the slurry and water separately to a second crystallizer to crystallize substantially the whole amount of the TBA (third aspect).

DETAILED DESCRIPTION OF THE INVENTION

The methanolic TBA solution (or TBA solution in methanol) used in the present invention is not limited in composition but usually contains 10 to 30% by weight of TBA and 70 to 90% by weight of methanol, based on the amount of the methanolic TBA solution. The solution may contain small amounts of water and brominated organic matter.

The methanolic TBA solution suited to the present invention is a liquid prepared by brominating BPA in a methanolic solvent with bromine and treating excess bromine with a reducing agent, such as hydrazine. The term "methanolic solvent" as used herein is intended to mean a solvent mainly comprising methanol. Therefore, the methanolic solvent can contain other components that do not directly participate in the bromination, such as water. For example, the "methanolic solvent" can be absolute methanol and an aqueous methanol solution having a water content of 15% by weight or less based on the amount of the aqueous methanol solution. BPA is dissolved in the methanolic solvent, and bromine is added in excess over a stoichiometric amount to produce TBA. If the water content of the methanolic solvent exceeds 15% by weight, part of produced TBA tends to crystallize while taking up bromine during the bromination reaction only to provide colored TBA crystals.

While not limiting, the BPA concentration in the methanolic solvent is usually 5 to 30% by weight based on methanolic solvent. The bromination temperature is usually 30° C. or lower. Bromine is usually used in an amount of 4 to 5 mol, preferably 4.1 to 4.5 mol, per mole of BPA. Containing excess bromine, the bromination reaction mixture is generally treated with a reducing agent to convert excess bromine into hydrogen bromide. Useful reducing agents include nitrogen-containing reducing agents, such as hydrazine and hydroxylamine; sulfur-containing reducing agents, such as sulfides, hydrosulfides, sulfur, sulfites, hydrosulfites, dithionites, and sulfurous acid gas; and hydrides, such a sodium borohydride. These reducing agents can be used either individually or a mixture of two or more thereof. The reducing agent can be used in the form of an aqueous solution. Preferred reducing agents include those which have high reducing power, need not be used in a large amount, and do not cause TBA to crystallize, such as hydrazine. The reaction mixture after reduction generally comprises 10 to 25% by weight of TBA, 0.5 to 1% by weight of tribromobisphenol A, 5 to 15% by weight of hydrobromic acid, 0 to 7% by weight of water, and 52 to 84% by weight of methanol, based on the amount of the reaction mixture. A small amount of side reaction products, such as tribromophenol, is also present.

The method according to the first aspect of the present invention essentially comprises separately feeding a methanolic TBA solution and water to a first crystallizer to obtain a slurry in which a part of the TBA is crystallized.

Water acts as a poor solvent for TBA crystallization. The amount of TBA to be crystallized is adjustable by the amount of water added. Addition of a large amount of water brings about an increased TBA crystallization ratio but suppresses crystal growth to provide small crystal grains with a slightly reduced purity. Where the amount of water is small, the crystal growth of TBA is improved to easily provide single crystals of 200 $\mu$m or greater, and the crystal purity is also improved, but the TBA crystallization ratio decreases in turn. Water added here corresponds to the water concentration of the mother liquor in the crystallizer so that the amount of water to be added is preferably decided based on this water concentration. The term "mother liquor" as used herein refers to the liquid phase of the crystallization slurry. As a matter of course the water content of the methanolic TBA solution contributes to the water concentration of the mother liquor.

The water concentration of the mother liquor is the greatest factor influential on the TBA crystallization ratio in the first crystallizer. The TBA crystallization ratio in the first crystallizer is desirably controlled between 70 and 95% by weight and, for this, the water concentration of the mother liquor is preferably adjusted to 12 to 35% by weight based on the amount of the mother liquor. The term "crystallization ratio" as used herein denotes the weight ratio of crystallized TBA to the TBA dissolved in the methanolic TBA solution, which is determined easily from the amount of water added, the water concentration of the mother liquor, and the TBA concentration of the mother liquor.

Within the TBA crystallization ratio range of from 70 to 95% by weight, there are obtained with ease high purity TBA single crystals having a grain size of 100 to 400 $\mu$m, which will serve as seed crystals in the second stage of crystallization in a second crystallizer to provide grown TBA crystals of high quality in a high recovery while suppressing nucleation. If the water concentration of the mother liquor is low, and the TBA crystallization ratio in the first stage of crystallization is lower than 70% by weight, the load of crystallization in the second crystallizer increases, the crystal size would become too large, and crystallites or agglomerates are formed in the second crystallizer to reduce filterability and purity. If, on the other hand, the water concentration of the mother liquor is high, and the TBA crystallization ratio exceeds 95% by weight, the resulting crystals are small and ready to agglomerate to reduce the purity. Note that the TBA crystallization ratio is influenced by not only the water concentration of the mother liquor but the composition of the methanolic TBA solution or the composition of the filtrate, so that it is difficult to decide the crystallization ratio only from the water concentration of the mother liquor.

While not limiting, the crystallizing temperature is preferably 10 to 40° C., still preferably 20 to 35° C. At lower temperatures crystal growth is suppressed to produce smaller grains. It tends to follow that the TBA crystals show poor filterability, needing an extended filtration time and resulting in reduction of crystal washing efficiency (leading to reduction in quality). At higher temperatures, crystal growth is accelerated, but problems tend to occur such as evaporation of methanol, induction of reaction between methanol and hydrogen bromide to form methyl bromide, and dissipation of a reducing gas, such as sulfurous acid gas, in case a reducing agent is used.

The crystallizing system is agitated to such a degree that the TBA slurry may flow uniformly.

The slurry residence time in the first crystallizer is usually 0.5 to 10 hours, preferably 1 to 5 hours. A short residence time attains high productivity but limits crystal growth, and the system tends to form crystallites and agglomerates. A long residence time secures satisfactory crystal growth to provide large TBA crystal grains. However, a residence time exceeding 5 hours hardly brings about further crystal growth and rather results in reduction of productivity and requires large-scaled equipment, which is industrially disadvantageous.

The TBA slurry in which a part of TBA is crystallized, which is obtained in the first crystallizer, can be withdrawn continuously, or when the crystallizer is filled to its capacity, the whole or a part of the slurry can be discharged. The former is a continuous feed and continuous discharge system, and the latter is a continuous feed and intermittent discharge system (semibatch system). The former system is preferred from the standpoint of operating properties and productivity.

Thus, in the first crystallizer, single crystals of TBA having a crystal size of 100 to 400 $\mu$m can be obtained efficiently. The crystals have high purity, having a low APHA (American Public Health Association) color number in an alkaline solution and containing substantially no impurities such as hydrolyzable bromine. Reduction in both the APHA color number and the hydrolyzable bromine content is required of a flame retardant for synthetic resins. The TBA crystallization ratio attained in this first stage crystallization is not high, which is compensated for in the second stage crystallization.

That is, the method according to the first aspect of the present invention essentially comprises continuously and simultaneously feeding the TBA slurry from the first crystallizer and water separately to a second crystallizer to crystallize substantially the whole amount of the TBA.

The language "substantially the whole amount of the TBA" is intended to mean that the crystallization ratio achieved is 97% by weight or higher, preferably 99% by weight or higher, still preferably 99.0 to 99.9% by weight, based on the TBA supplied to the first crystallizer, which is the industrially possible highest level of crystallization. The crystallization ratio reached chiefly depends on the amount of water added, i.e., the water concentration of the mother liquor. A higher water concentration leads to a higher crystallization ratio, and vise versa. A water concentration for obtaining a crystallization ratio of 99.0 to 99.9% by weight is usually 40 to 60% by weight based on the amount of the mother liquor. When the crystallization ratio is low, the TBA crystals grow well in the second crystallizer without being accompanied by nucleation, but the recovery is low, which is slightly against economies. When the crystallization ratio is high, the recovery increases to improve economies, but the crystal growth of TBA is suppressed, tending to cause nucleation, which can result in formation of crystallites or agglomerates. The TBA crystallization ratio is easily obtained from the amount of water added, the water concentration of the mother liquor, and the TBA concentration of the mother liquor.

The crystallizing temperature in the second crystallizer is usually 10 to 40° C., preferably 20 to 40° C., still preferably 20 to 30° C., for the same reasons as described with respect to the first stage crystallization.

The crystallizing system is agitated to such a degree that the TBA slurry may flow uniformly.

The slurry residence time in the second crystallizer is usually 0.3 to 5 hours, preferably 0.5 to 2 hours. Because the amount of TBA precipitated in the second crystallizer is smaller than that in the first one, while the amount of the TBA crystals (the surface area of the crystals) present in the second one is large, the TBA crystals fed from the first crystallizer are allowed to grow while preventing nucleation even in a shorter residence time. Further, a shorter residence time has another advantage that incorporation of impurities can be suppressed thereby to reduce the alkaline solution APHA color number and to minimize the hydrolyzable bromine content. This is a significant finding reached by the present inventors. It should be noted that too short a residence time allows formation of crystallites or agglomerates and that too long a residence time necessitates large-scaled equipment and tends to deteriorate the quality.

Similarly to the first stage crystallization, the crystallization in the second stage can be conducted either in a system of continuous feed of TBA slurry and water, and continuous discharge of TBA slurry or in a continuous feed and intermittent discharge system (semibatch system). The former system is preferred from the standpoint of operating properties, productivity and crystal purity.

The crystallizers used in the first and the second crystallization stages include a stirred tank type, a draft tube type, and a classifying type.

In a modification of the above-described method, three or more crystallizers can be used to attain a further increased crystallization ratio. The crystallization ratio to be achieved can be appropriately allotted to the first and the second crystallizers or three or more crystallizers.

High purity TBA single crystals of 100 to 400 $\mu$m can thus be obtained in high yield.

The resulting TBA crystal slurry is separated into a wet cake of TBA and a filtrate by a centrifugal filter, a pressure filter, etc. A centrifugal filter is preferred for minimizing crystal breakage and improving washing efficiency. The TBA wet cake is preferably washed with a mixed solvent of methanol and water to thoroughly remove the surface mother liquor while preventing the TBA crystals from dissolving. The washed crystals are then dried in a usual manner, such as through-flow drying or vacuum drying to obtain a TBA product.

In the second aspect of the present invention, a methanolic TBA solution containing bromine can be crystallized as such. That is, the method according to the second aspect of the present invention essentially comprises continuously and simultaneously feeding a methanolic TBA solution containing bromine, water, and a reducing agent separately to a crystallizer to cause the TBA to crystallize and to cause bromine to be reduced simultaneously. According to this method, TBA crystals can be obtained manageably and economically.

The term "methanolic TBA solution containing bromine (or bromine-containing methanolic TBA solution)" as used herein denotes a solution containing bromine, TBA and methanol as main components, usually comprising 1 to 5% by weight of bromine, 10 to 30% by weight of TBA and 65 to 89% by weight of methanol, based on the amount of methanolic TBA solution containing bromine. The solution can contain small amounts of water and brominated organic matter. A bromine-containing methanolic TBA solution to which the present invention is preferably applied is the reaction mixture obtained by brominating BPA in a methanolic solvent with bromine.

The term "methanolic solvent" has the same meaning as defined above and includes, for example, absolute methanol and an aqueous methanol solution having a water content of 15% by weight or less based on the amount of the aqueous methanol solution. BPA is dissolved in the methanolic solvent, and bromine is added in excess over a stoichiometric amount to produce TBA. If the water content of the methanolic solvent exceeds 15% by weight, part of produced TBA tends to crystallize, and the resultant TBA crystals may take up bromine during the bromination reaction to get colored.

While not limiting, the BPA concentration in the methanolic solvent is usually 5 to 30% by weight based on methanolic solvent. The bromination temperature is usually 30° C. or lower so as to suppress co-production of methyl bromide from methanol and by-produced hydrogen bromide. Bromine is usually used in an amount of 4.0 to 5.0 mol, preferably 4.1 to 4.5 mol. per mole of BPA. At a Br/BPA molar ratio less than 4.0, the yield of TBA reduces. At a Br/BPA molar ratio more than 5.0, excess bromine is liable to induce side reactions. The thus prepared bromine-containing methanolic TBA solution typically comprises 10 to 25% by weight of TBA, 0.5 to 1% by weight of tribromobisphenol A, 5 to 15% by weight of hydrobromic acid, 0 to 5% by weight of water, 1 to 5% by weight of residual bromine, and 55 to 75% by weight of methanol based on the amount of the bromine-containing methanolic TBA solution.

The way of separately, continuously and simultaneously feeding the bromine-containing methanolic TBA solution, a reducing agent, and water to a crystallizer is not particularly restricted. For example, each of them can be fed by use of a common constant rate pump. The crystallizer includes, but is not limited to, continuous crystallizers, such as transport type crystallizers, e.g., a draft-tube baffled type crystallizer and a double propeller type crystallizer, common stirred tank type crystallizers, and classifying crystallizers, such as a Crystal-Oslo crystallizer.

Any reducing agents capable of reducing bromine to hydrogen bromide can be used. Suitable reducing agents include nitrogen-containing reducing agents, such as hydrazine and hydroxylamine; sulfur-containing reducing agents, such as sulfides, hydrosulfides, sulfur, sulfites, hydrosulfites, dithionites, and sulfurous acid gas; and hydrides, such a sodium borohydride. These reducing agents can be used either individually or a mixture of two or more thereof. It is preferred to use at least one reducing agent selected from the group consisting of hydrazine, sodium sulfite, sodium hydrosulfite, sodium dithionite, and sulfurous acid gas from the standpoint of reactivity with bromine, quality of TBA crystals, availability, manageability, and economy. These preferred reducing agents exhibit strong reducing power to reduce residual bromine to hydrogen bromide quickly. The concentration of the reducing agent is not limited, and either a saturated aqueous solution or a dilute aqueous solution can be used. Sulfurous acid gas may be introduced as such.

The amount of the reducing agent to be fed could be slightly less than an equivalent to residual bromine in the methanolic TBA solution, e.g., about 0.95 equivalent, but is preferably equivalent or more to the residual bromine so that the residual bromine may completely be converted into hydrogen bromide to produce TBA crystals of higher quality. A preferred amount of the reducing agent is 1.05 to 1.30 equivalent to the residual bromine.

An oxidation-reduction reaction takes plate between the reducing agent and residual bromine. In using hydrazine as a reducing agent, the reaction proceeds as follows.

$$N_2H_4 + 2Br_2 \rightarrow 4HBr + N_2$$

In using sodium sulfite, the follow reaction goes.

$$Na_2SO_3 + Br_2 + H_2O \rightarrow 2HBr + Na_2SO_4$$

While the control on the amount of the reducing agent added can be made by means of a constant rate pump, it is a preferred embodiment to control the feed of the reducing agent based on the oxidation-reduction (redox) potential of the mother liquor during TBA crystallization. The latter control is preferred for ease of operation and high precision. The redox potential is preferably controlled to 600 mV (vs. SCE) or less. Under this condition bromine has been converted to hydrogen bromide completely, leaving no residual bromine in the mother liquor, and bromine does not enter the precipitated crystals, to provide high quality TBA crystals. When the amount of the reducing agent added is less than the reducing equivalent, a higher redox potential than 600 mV is shown, indicating that part of bromine remains non-reduced. Part of the remaining bromine can enter the TBA crystals to slightly reduce the quality. Addition of the reducing agent more than necessary, while having no adverse influence on the crystal quality, is nothing but a false economy. The above-specified preferred amount of the reducing agent (1.05 to 1.30 equivalent) corresponds to a redox potential of about 550 to 400 mV. The redox potential is measured by using a generally employed oxidation-reduction electrode, such as a platinum electrode or a gold electrode, coupled with a reference electrode, or a composite electrode (a combination of a redox electrode and a reference electrode).

Water is added continuously and simultaneously with the reducing agent. Since water acts as a poor solvent for TBA crystallization, the amount of TBA to be crystallized is adjustable by the amount of water added. When a large amount of water is added, the recovery of TBA crystals increases to 99% by weight or higher and can reach 99.9% by weight, based on the TBA supplied, but suppresses crystal growth to provide small crystals with a slightly reduced purity. Where the amount of water is small, the crystal growth is improved to produce single crystals of 200 μm or larger with ease, and the crystal purity is also improved, but the recovery decreases.

Water added corresponds to the water concentration of the mother liquor in the crystallizer so that the amount of water to be added is preferably decided based on this water concentration. As a matter of course the water content of the bromine-containing methanolic TBA solution or the water content of reducing solution contributes to the water concentration of the mother liquor. The water concentration of the mother liquor is decided appropriately according to a desired TBA recovery or a desired degree of crystal growth. For ease of operation, a water concentration of 20 to 60% by weight based on the amount of the mother liquor would be suitable.

While water is in principle added separately from the bromine-containing methanolic TBA solution and the reducing agent, a part or the whole of water may be added previously to the bromine-containing methanolic TBA solution or the reducing agent. When previously added to the methanolic TBA solution, the amount of water must be within such that does not cause TBA to crystallize. Where the reducing agent is water soluble, the whole amount of water could be added thereto beforehand. Thus, the bromine-containing methanolic TBA solution, the reducing agent and water are separately, continuously and simultaneously fed to a crystallizer, where reduction of bromine and crystallization of TBA are carried out simultaneously.

While not limiting, the crystallizing temperature is preferably 10 to 40° C., still preferably 20 to 35° C. At lower temperatures crystal growth is suppressed to produce smaller crystals. It tends to follow that the TBA crystals have poor filterability, needing an extended filtration time and resulting in reduction of crystal washing efficiency (leading to reduction in quality). At higher temperatures, crystal growth is accelerated, but problems tend to occur such as evaporation of methanol and dissipation of a reducing gas, such as sulfurous acid gas.

The reducing and crystallizing system is agitated to such a degree that the TBA slurry may flow uniformly.

The slurry residence time in the crystallizer is usually 0.5 to 10 hours, preferably 1 to 5 hours. A short residence time attains high productivity but limits crystal growth. A long residence time secures satisfactory crystal growth to provide large TBA crystals. However, a residence time exceeding 5 hours hardly brings about further crystal growth and rather results in appreciable reduction of productivity.

The resulting TBA slurry can be withdrawn continuously, or when the vessel is filled to its capacity, the whole or a part of the slurry can be discharged. The former is a continuous feed and continuous discharge system, and the latter is a continuous feed and intermittent discharge system (semibatch system). The former system is preferred from the standpoint of operating properties and productivity.

The withdrawn TBA crystal slurry is usually separated into a wet cake of TBA and a filtrate by means of a centrifugal filter, a pressure filter, etc. A centrifugal filter is preferred for minimizing crystal breakage and improving washing efficiency. The TBA wet cake is preferably washed with a mixed solvent of methanol and water to thoroughly remove the surface mother liquor while preventing the TBA crystals from dissolving. The washed crystals are then dried in a usual manner to obtain a TBA product.

The present invention further provides in its third aspect a manageable and economical method for crystallizing TBA, which essentially comprises continuously and simultaneously feeding a methanolic TBA solution containing bromine, a reducing agent, and water separately to a first crystallizer to obtain a slurry in which a part of the TBA is crystallized and continuously and simultaneously feeding the slurry and water separately to a second crystallizer to crystallize substantially the whole amount of the TBA.

The term "methanolic TBA solution containing bromine (bromine-containing methanolic TBA solution)", inclusive of the term "methanolic solvent" attendant thereon, as used herein is the same as defined with respect to the second aspect of the invention. Description of the second aspect about a typical composition of the bromine-containing methanolic TBA solution, an example of the methanolic solvent, and a bromine-containing methanolic TBA solution to which the present invention is preferably applied also applies to the third aspect unless otherwise specified.

In the first stage of crystallization, the bromine-containing methanolic TBA solution, a reducing agent, and water are separately, continuously and simultaneously fed to a first crystallizer to obtain a slurry in which a part of the TBA is crystallized.

Water acts as a poor solvent for TBA crystallization. The amount of TBA to be crystallized is adjustable by the amount of water added. Addition of a large amount of water brings an increased TBA crystallization ratio but suppresses crystal growth to provide small crystal grains with a slightly reduced purity. Where the amount of water is small, the crystal growth is improved to produce single crystals of 200 $\mu$m or greater with ease, and the crystal purity is also improved, but, in turn, the TBA crystallization ratio decreases. Water added here corresponds to the water concentration of the mother liquor in the first crystallizer so that the amount of water to be added is preferably decided based on this water concentration. As a matter of course the water content of the bromine-containing methanolic TBA solution contributes to the water concentration of the mother liquor.

The water concentration of the mother liquor is the greatest factor influential on the TBA crystallization ratio in the first crystallizer. The TBA crystallization ratio in the first crystallizer is desirably controlled between 70 and 95% by weight and, for this, the water concentration of the mother liquor is preferably adjusted to 12 to 35% by weight based on the amount of the mother liquor. The TBA crystallization ratio is determined easily from the amount of water added, the water concentration of the mother liquor, and the TBA concentration of the mother liquor.

Within the TBA crystallization ratio range of from 70 to 95% by weight, there are obtained with ease high purity TBA single crystals having a grain size of 100 to 400 $\mu$m, which will serve as seed crystals in the second stage of crystallization in a second crystallizer to provide grown TBA crystals of high quality at a high recovery while suppressing nucleation. If the water concentration of the mother liquor is low, and the TBA crystallization ratio in the first stage of crystallization is lower than 70% by weight, the load of crystallization in the second crystallizer increases, the crystal size would become too large, and crystallites or agglomerates are formed in the second crystallizer to reduce filterability and purity. If, on the other hand, the water concentration of the mother liquor is high, and the TBA crystallization ratio exceeds 95% by weight, the resulting crystals are small and ready to agglomerate to reduce the purity. Note that the TBA crystallization ratio is influenced by not only the water concentration of the mother liquor but the composition of the bromine-containing methanolic TBA solution, the composition of the filtrate, and the reducing agent, so that it is difficult to decide the crystallization ratio only from the water concentration of the mother liquor.

Any reducing agent capable of reducing bromine to hydrogen bromide can be used. Suitable reducing agents include nitrogen-containing reducing agents, such as hydrazine and hydroxylamine; sulfur-containing reducing agents, such as sulfides, hydrosulfides, sulfur, sulfites, hydrosulfites, dithionites, and sulfurous acid gas; and hydrides, such a sodium borohydride. These reducing agents can be used either individually or a mixture of two or more thereof. They can be used in the form of an aqueous solution. It is preferred to use at least one reducing agent selected from the group consisting of hydrazine, sodium sulfite, sodium hydrosulfite, sodium dithionite, and sulfurous acid gas from the standpoint of reactivity with bromine, quality of TBA crystals, availability, manageability, and economy. These preferred reducing agents exhibit strong reducing power to reduce residual bromine to hydrogen bromide quickly. The concentration of the reducing agent is not limited, and either a saturated aqueous solution or a dilute aqueous solution can be used. Sulfurous acid gas may be introduced as such.

The amount of the reducing agent to be added can be slightly less than an equivalent to residual bromine in the bromine-containing methanolic TBA solution, e.g., about 0.95 equivalent, but is preferably one equivalent or more to the residual bromine so that the residual bromine may completely be converted into hydrogen bromide to produce TBA crystals of higher quality. A preferred amount of the reducing agent is 1.05 to 1.30 equivalent to the residual bromine.

While the control on the amount of the reducing agent added can be made by means of a constant rate pump, it is a preferred embodiment to control the feed of the reducing agent based on the redox potential of the mother liquor during TBA crystallization. The latter control is preferred for ease of operation and high precision. The redox potential is preferably controlled to 600 mV (vs. SCE) or less. Under this condition bromine has been converted to hydrogen bromide completely, leaving no bromine in the mother liquor, and bromine does not enter the precipitated crystals, to provide high quality TBA crystals. When the amount of the reducing agent added is less than the reducing equivalent, a higher redox potential than 600 mV is shown, indicating that part of bromine remains non-reduced. Part of the remaining bromine can enter the TBA crystals to slightly reduce the quality. Addition of the reducing agent more than necessary, while having no adverse influence on the crystal quality, is nothing but a false economy. The above-specified preferred amount of the reducing agent (1.05 to 1.30 equivalent) corresponds to a redox potential of about 550 to 400 mV.

While water is in principle added separately from the methanolic TBA solution and the reducing agent, a part or the whole of water may be added previously to the bromine-containing methanolic TBA solution or the reducing agent. When previously added to the bromine-containing methanolic TBA solution, the amount of water must be within such that does not cause TBA to crystallize. Where the reducing agent is water soluble, the whole amount of water could be added thereto beforehand.

While not limiting, the crystallizing temperature is preferably 10 to 40° C., still preferably 20 to 35° C. At lower temperatures crystal growth is suppressed to produce smaller crystals. It tends to follow that the TBA crystals have poor filterability, needing an extended filtration time and resulting in reduction of crystal washing efficiency (leading to reduction in quality). At higher temperatures, crystal growth is accelerated, but problems tend to occur such as evaporation of methanol, induction of reaction between methanol and hydrogen bromide to form methyl bromide, and dissipation of a reducing gas, such as sulfurous acid gas.

The crystallizing system is agitated to such a degree that the TBA slurry may flow uniformly.

The slurry residence time in the first crystallizer is usually 0.5 to 10 hours, preferably 1 to 5 hours. A short residence time attains high productivity but limits crystal growth, readily allowing formation of crystallites or agglomerates. A long residence time secures satisfactory crystal growth to provide large TBA crystals. However, a residence time exceeding 5 hours hardly brings about further crystal growth, rather results in reduction of productivity, and requires large-scaled equipment, which is industrially disadvantageous.

The resulting TBA slurry can be withdrawn from the first crystallizer continuously, or when the vessel is filled to its capacity, the whole or a part of the slurry can be discharged. The former is a continuous feed and continuous discharge system, and the latter is a continuous feed and intermittent discharge system (semibatch system). The former system is preferred from the standpoint of operating properties and productivity.

Thus, in the first crystallizer, single crystals of TBA having a crystal size of 100 to 400 $\mu$m can be obtained efficiently. Having a high purity, the crystals have a low APHA color number (in an alkaline solution) and contain substantially no impurities such as hydrolyable bromine. To have a low APHA color number and a low hydrolyzable bromine content are properties required of a flame retardant for use in synthetic resins. Although the crystallization ratio achieved in this first stage of crystallization is not high, it is compensated for in the second stage crystallization.

That is, the method of the third aspect of the present invention essentially comprises separately, continuously and simultaneously feeding the TBA slurry obtained from the first crystallizer and water to a second crystallizer to crystallize substantially the whole amount of the TBA.

What is meant by "crystallization of substantially the whole amount of the TBA" and its preferred embodiment are the same as explained above with respect to the second aspect of the invention. The crystallization ratio can be adjusted chiefly by the amount of water added, i.e., the water concentration of the mother liquor. A higher water concentration leads to a higher crystallization ratio, and vise versa. A water concentration for obtaining the preferred crystallization ratio (99.0 to 99.9% by weight) is usually 40 to 60% by weight based on the amount of the mother liquor. When the crystallization ratio is low, the TBA crystals grow well in the second crystallizer without being accompanied by nucleation, but the recovery is low, which is slightly against economies. When the crystallization ratio is high, the recovery increases to improve economies, but the crystal growth is suppressed, tending to cause nucleation, which can result in formation of crystallites or agglomerates. The TBA crystallization ratio is easily obtained from the amount of water added, the water concentration of the mother liquor, and the TBA concentration of the mother liquor.

The crystallizing temperature in the second crystallizer is usually 10 to 40° C., preferably 20 to 40° C., still preferably 20 to 30° C., for the same reasons as described with respect to the first stage crystallization.

The crystallizing system is agitated to such a degree that the TBA slurry may flow uniformly.

The slurry residence time is usually 0.3 to 5 hours, preferably 0.5 to 2 hours. Because the amount of TBA precipitated in the second crystallizer is smaller than that in the first one, while the amount of the TBA crystals (the surface area of the crystals) present in the second one is large, the TBA crystals fed from the first crystallizer are allowed to grow while preventing nucleation even in a shorter residence time. It should be noted that too short a residence time allows formation of crystallites or agglomerates and that too long a residence time necessitates large-scaled equipment and tends to deteriorate the quality.

Similarly to the first stage crystallization, the crystallization in the second stage can be conducted either in a system of continuous feed of the TBA slurry and water, and continuous discharge of the TBA slurry or in a continuous feed and intermittent discharge system (semibatch system). The former system is preferred from the standpoint of operating properties, productivity and crystal purity.

The crystallizers used in the first and the second crystallization stages include a stirred tank type, a draft tube type, and a classifying type.

In a variant of the third aspect of the invention, three or more crystallizers can be used to attain a further increased crystallization ratio. The crystallization ratio to be achieved can be appropriately allotted to the first and the second crystallizers or three or more crystallizers.

High purity TBA single crystals of 100 to 400 $\mu$m can thus be produced in high yield. The resulting TBA crystal slurry is separated into a wet cake of TBA and a filtrate by a centrifugal filter, a pressure filter, etc. A centrifugal filter is preferred for minimizing crystal breakage and improving washing efficiency. The TBA wet cake is preferably washed with a mixed solvent of methanol and water to thoroughly remove the surface mother liquor while preventing the TBA crystals from dissolving. The washed crystals are then dried in a usual manner, such as through-flow drying or vacuum drying to obtain a TBA product.

The present invention will now be illustrated in greater detail with reference to Examples, but it should be understood that the invention is not construed as being limited thereto. TBA crystals obtained in Examples and Comparative Examples were evaluated as follows.

(1) APHA color number (in alkaline solution)

TBA crystals weighing 17 g were dissolved in 80 ml of a 1.5N aqueous solution of sodium hydroxide, followed by stirring at 30° C. for 15 minutes. The alkaline TBA solution was analyzed by colorimetry using APHA color number standard solutions.

(2) Hydrolyzable bromine

TBA crystals were dissolved in a 0.1N potassium hydroxide solution in methanol, and the solution was heated to 70° C. for 15 minutes. The amount of released bromide ions was measured by potentiometric titration using an aqueous silver nitrate reference solution. The amount of free bromide ions (also designated inorganic bromide ions) separately determined was subtracted from the measured value to give a hydrolyzable bromine content in terms of ppm based on the weight of TBA. The inorganic bromide ion content, represented in terms of ppm based on the weight of TBA, is obtained by analyzing free bromide ion in an acetone solution of TBA by potentiometric titration with an aqueous silver nitrate solution.

(3) Crystal purity

A solution of TBA crystals dissolved in a solvent was analyzed by HPLC using a reversed phase chromatography column (TSK-gel ODS-120T manufactured by TOSOH CORPORATION) and eluent (50 mmol-$KH_2PO_4$/$CH_3CN$ (pH=3.0)=47/53 (vol/vol)) and detected with a UV detector. The crystal purity was calculated from the peak area ratio of each peak at 245 nm.

(4) Bromine content in TBA crystals

TBA crystals were dissolved in chlorobenzene and washed with a 0.1 wt % aqueous sulfuric acid solution. Free bromine in chlorobenzene was reduced with an aqueous hydrazine solution and extracted into the aqueous layer as bromide ion, which was determined by potentiometric titration with an aqueous silver nitrate solution.

(5) APHA color number in methanol

A 20 wt % solution of TBA crystals in methanol was analyzed by colorimetry using APHA color number standard solutions.

Bromine content in solution obtained in Examples and Comparative Examples was evaluated as follows.

A 5 wt % aqueous potassium iodide solution was added to a solution under analysis. The released iodine was determined by titration with a 0.1N aqueous sodium dithionite solution using an aqueous starch solution as an indicator.

REFERENCE EXAMPLE

Preparation of methanolic TBA solution:

To a 3-liter jacketed separable flask equipped with an agitator, a thermometer and a discharge outlet were continuously and simultaneously fed a 12 wt % methanolic solution of BPA (water content: 3.5 wt %) and bromine at a rate of 280 g/hr and 100 g/hr, respectively, while maintaining the liquid temperature at 15° C. The reaction mixture (methanolic solution containing excess bromine) was continuously discharged while keeping the amount of the liquid in the flask at 2.3 kg, which was used in Examples 2 and 8 to 11 and Comparative Examples 2 to 4.

Excess bromine in the reaction mixture was reduced with hydrazine to obtain a methanolic TBA solution, which was used in Examples 1 and 3 to 7 and Comparative Example 1. The methanolic TBA solution after reduction consisted of 20.1 wt % of TBA, 0.5 wt % of tribromobisphenol A, 14.2 wt % of hydrobromic acid, 2.7 wt % of water, and 62.5 wt % of methanol.

Example 1

Into a 3-liter glass-made first crystallizer and a 1-liter glass-made second crystallizer, both jacketed and equipped with a thermometer, an agitator, a cooler, and a discharge outlet, were put 2031 g and 1039 g, respectively, of the methanolic TBA solution and stirred. Constant temperature water was circulated through each jacket to maintain the liquid temperature at 30° C. The methanolic TBA solution and water were continuously and simultaneously fed to the first crystallizer at a rate of 600 g/hr and 77 g/hr, respectively, and the resulting TBA slurry was continuously discharged from the outlet at a rate corresponding to the total fed amount of the methanolic TBA solution and water and introduced into the second crystallizer. At the same time, 362 g/hr of water was continuously fed to the second crystallizer, and the resulting TBA slurry was continuously withdrawn from the second crystallizer at a rate corresponding to the total fed amount of the TBA slurry and water. After 12-hour continuous operation, the slurry withdrawn from the second crystallizer was separated into a wet cake and a filtrate. The wet cake was washed with an aqueous methanol solution and dried at 90° C. for 2 hours to obtain dry TBA crystals. The residence times in the first crystallizer and the second crystallizer were 3.0 hours and 1.0 hour, respectively, and the crystallization ratios based on the TBA supplied were 89.0 wt % and 99.7 wt %, respectively. The mother liquor in the first and the second crystallizers had a water concentration of 16.3 wt % and 54.5 wt %, respectively. The dry TBA crystals recovered from the second crystallizer were single crystals having an average particle size of 250 $\mu$m and had an APHA color number of 24 in an alkaline solution and a hydrolyzable bromine content of 10 ppm (by weight).

Example 2

Into a 3-liter glass-made first crystallizer and a 1-liter glass-made second crystallizer, both jacketed and equipped with a thermometer, an agitator, a cooler, a redox electrode, and a discharge outlet, were put 2031 g and 1039 g, respectively, of the methanolic TBA solution and stirred. Constant temperature water was circulated through each jacket to maintain the liquid temperature at 30° C. The bromine-containing methanolic TBA solution, water, and a 14 wt % aqueous solution of sodium sulfite were continuously and simultaneously fed to the first crystallizer at a rate of 600 g/hr, 18 g/hr, and 69 g/hr (corresponding to 1.07 equivalent to bromine), respectively, and the resulting TBA slurry was continuously discharged from the outlet at a rate corresponding to the total fed amount of the bromine-containing methanolic TBA solution, water, and the reducing agent and introduced into the second crystallizer. At the same time, 362 g/hr of water was continuously fed to the second crystallizer, and the resulting TBA slurry was continuously withdrawn from the second crystallizer at a rate corresponding to the total fed amount of the TBA slurry and water. The redox potential in the first crystallizer was between 470 and 480 mV (vs. SCE). After 12-hour continuous operation, the slurry withdrawn from the second crystallizer was separated into a wet cake and a filtrate. The wet cake was washed with an aqueous methanol solution and dried at 90° C. for 2 hours to obtain dry TBA crystals. The residence times in the first crystallizer and the second crystallizer were 3.0 hours and 1.0 hour, respectively, and the crystallization ratios based on the TBA supplied were 89.0 wt % and 99.7 wt %, respectively. The mother liquor in the first and the second crystallizers had a water concentration of 18.3 wt % and 54.3 wt %, respectively. The dry TBA crystals recovered from the second crystallizer were single crystals having an average particle size of 250 $\mu$m and had an APHA color number of 26 in an alkaline solution and a hydrolyzable bromine content of 19 ppm (by weight).

Example 3

Continuous crystallization of TBA was carried out in the same equipment in the same manner as in Example 1, except that 870 g/hr of the methanolic TBA solution and 112 g/hr of water were continuously and simultaneously fed to the first crystallizer and that 518 g/hr of water was continuously fed to the second crystallizer. The TBA slurry continuously discharged from the second crystallizer was worked up in the same manner as in Example 1 to obtain TBA crystals. The residence times in the first crystallizer and the second crystallizer were 2.1 hours and 0.5 hour, respectively, and the crystallization ratios based on the TBA supplied were 89.7 wt % and 99.8 wt %, respectively. The mother liquor in the first and the second crystallizers had a water concentration of 18.2 wt % and 55.5 wt %, respectively. The dry TBA crystals recovered from the second crystallizer were 100% pure single crystals having an average particle size of 230 $\mu$m and had an APHA color number of 31 in an alkaline solution and a hydrolyzable bromine content of 12 ppm (by weight).

Example 4

Continuous crystallization of TBA was carried out in the same equipment in the same manner as in Example 1, except that 1070 g/hr of the methanolic TBA solution and 127 g/hr of water were continuously and simultaneously fed to the first crystallizer and that 600 g/hr of water was continuously fed to the second crystallizer. The TBA slurry continuously discharged from the second crystallizer was worked up in the same manner as in Example 1 to obtain TBA crystals. The residence times in the first crystallizer and the second crystallizer were 1.2 hour and 0.8 hour, respectively, and the crystallization ratios based on the TBA supplied were 89.1 wt % and 99.7 wt %, respectively. The mother liquor in the first and the second crystallizers had a water concentration of 17.3 wt % and 55.9 wt %, respectively. The dry TBA crystals recovered from the second crystallizer were single crystals having an average particle size of 220 $\mu$m and had a purity of 99.9% (by area), an APHA color number of 29 in an alkaline solution and a hydrolyzable bromine content of 16 ppm (by weight).

Example 5

Continuous crystallization of TBA was carried out in the same equipment in the same manner as in Example 1, except that 937 g/hr of the methanolic TBA solution and 50 g/hr of water were continuously and simultaneously fed to the first crystallizer and that 263 g/hr of water was continuously fed to the second crystallizer. The TBA slurry continuously discharged from the second crystallizer was worked up in the same manner as in Example 1 to obtain TBA crystals. The residence times in the first crystallizer and the second crystallizer were 1.9 hours and 2.5 hours, respectively, and the crystallization ratios based on the TBA fed were 86.5 wt % and 99.7 wt %, respectively. The mother liquor in the first and the second crystallizers had a water concentration of 15.4 wt % and 55.0 wt %, respectively. The dry TBA crystals recovered from the second crystallizer were single crystals having an average particle size of 220 $\mu$m and had a purity of 99.9% (by area), an APHA color number of 65 in an alkaline solution and a hydrolyzable bromine content of 52 ppm (by weight).

Example 6

Continuous crystallization of TBA was carried out in the same equipment in the same manner as in Example 1, except that 1366 g/hr of the methanolic TBA solution and 307 g/hr of water were continuously and simultaneously fed to the first crystallizer and that 827 g/hr of water was continuously fed to the second crystallizer. The TBA slurry continuously discharged from the second crystallizer was worked up in the same manner as in Example 1 to obtain TBA crystals. The residence times in the first crystallizer and the second crystallizer were 0.5 hour and 1.0 hour, respectively, and the crystallization ratios based on the TBA supplied were 90.0 wt % and 99.8 wt %, respectively. The mother liquor in the first and the second crystallizers had a water concentration of 18.3 wt % and 55.0 wt %, respectively. The dry TBA crystals recovered from the second crystallizer were single crystals having an average particle size of 200 $\mu$m and had a purity of 99.9% (by area), an APHA color number of 75 in an alkaline solution and a hydrolyzable bromine content of 75 ppm (by weight).

Example 7

Continuous crystallization of TBA was carried out in the same equipment in the same manner as in Example 1, except that 782 g/hr of the methanolic TBA solution and 176 g/hr of water were continuously and simultaneously fed to the first crystallizer and that 474 g/hr of water was continuously fed to the second crystallizer. The TBA slurry continuously discharged from the second crystallizer was worked up in the same manner as in Example 1 to obtain TBA crystals. The residence times in the first crystallizer and the second crystallizer were 1.0 hour and 1.0 hour, respectively, and the crystallization ratios based on the TBA supplied were 95.1 wt % and 99.8 wt %, respectively. The mother liquor in the first and the second crystallizers had a water concentration of 35.0 wt % and 54.9 wt %, respectively. The dry TBA crystals recovered from the second crystallizer were single crystals having an average particle size of 180 $\mu$m and had a purity of 99.9% (by area), an APHA color number of 68 in an alkaline solution and a hydrolyzable bromine content of 55 ppm (by weight).

Example 8

Continuous crystallization of TBA was carried out in the same equipment in the same manner as in Example 2. To the first crystallizer were continuously and simultaneously fed 600 g/hr of the bromine-containing methanolic TBA solution, 39 g/hr of water, and 68 g/hr of a 14 wt % aqueous solution of sodium sulfite (corresponding to 1.05 equivalent to bromine), and to the second crystallizer was fed 340 g/hr of water continuously. The redox potential in the first crystallizer was between 470 and 500 mV (vs. SCE). The TBA slurry continuously discharged from the second crystallizer was worked up in the same manner as in Example 2 to obtain TBA crystals. The residence times in the first crystallizer and the second crystallizer were 2.1 hours and 0.5 hour, respectively, and the crystallization ratios based on the TBA supplied were 92.0 wt % and 99.8 wt %, respectively. The mother liquor in the first and the second crystallizers had a water concentration of 20.0 wt % and 54.9 wt %, respectively. The dry TBA crystals recovered from the second crystallizer were single crystals having an average particle size of 230 μm and had a purity of 100% (by area), an APHA color number of 34 in an alkaline solution and a hydrolyzable bromine content of 26 ppm (by weight).

Comparative Example 1

Into a 2-liter jacketed glass-made crystallizer equipped with an agitator, a cooler, and a discharge outlet was put 1654 g of the methanolic TBA solution and stirred. Constant temperature water was circulated through the jacket to maintain the liquid temperature at 30° C. The methanolic TBA solution and water were continuously and simultaneously fed to the crystallizer at a rate of 888 g/hr and 766 g/hr, respectively, and the resulting TBA slurry was continuously discharged from the outlet at a rate corresponding to the total fed amount of the methanolic TBA solution and water. The slurry was separated into a wet cake and a filtrate, and the wet cake was washed with an aqueous methanol solution and dried at 90° C. for 2 hours to obtain dry TBA crystals. The residence time in the crystallizer was 1.0 hour, the crystallization ratio was 99.7 wt %, and the mother liquor in the crystallizer had a water concentration of 50 wt %. The dry TBA crystals were agglomerates having an average particle size of 100 μm and had an APHA color number of 100 in an alkaline solution and a hydrolyzable bromine content of 117 ppm (by weight).

Example 9

To a 1-liter jacketed glass-made crystallizer equipped with an agitator, a thermometer, a redox electrode, and a discharge outlet were separately fed 600 g/hr of the bromine-containing methanolic TBA solution, 360 g/hr of water, and 69 g/hr of a 14 wt % aqueous sodium sulfite solution (corresponding to 1.05 equivalent to bromine) in a continuous mode. The liquid temperature was kept at 30° C. by circulating constant temperature water through the jacket. The redox potential in the crystallizer was between 470 and 480 mV (vs. SCE). The resulting TBA slurry had a concentration of 11.7 wt %. The TBA recovery by crystallization was 99.7 wt %. The slurry was continuously discharged from the outlet and suction filtered through a Buchner funnel. The wet cake was washed with an aqueous methanol solution and dried to obtain dry TBA crystals. The resulting TBA crystals were white crystals having an average particle size of 100 μm and a purity of 99.6% (by area) with no bromine detected. The $SO_4^{2-}$ concentration was 0.1 ppm or less. A 20 wt % methanolic solution of the TBA crystals had an APHA color number of 10 or smaller.

Example 10

Crystallization of TBA was carried out in the same manner as in Example 9, except that a 32 wt % aqueous hydrazine solution was fed at a rate of 3.8 g/hr (corresponding to 1.05 equivalent to bromine) in place of the sodium sulfite solution. The operation was easy. The redox potential during crystallization was between 470 and 480 mV (vs. SCE). The TBA slurry concentration after crystallization was 12.6 wt %, and the TBA recovery by crystallization was 99.6 wt %. The resulting dry TBA crystals were white crystals having an average particle size of 100 μm and a purity of 99.7% (by area) with no bromine detected. A 20 wt % methanolic solution of the crystals had an APHA color number of 10 or smaller.

Example 11

Crystallization was carried out in the same manner as in Example 9, except for feeding sulfurous acid gas from a bomb at a rate of 1.7 l/hr (corresponding to 1.05 equivalent to bromine) in place of the sodium sulfite solution. The redox potential during crystallization was between 450 and 500 mV (vs. SCE). The operation for reduction and crystallization was easy to carry out. The TBA slurry concentration after crystallization was 12.5 wt %, and the TBA recovery by crystallization was 99.6 wt %. The resulting dry TBA crystals were white crystals having an average particle size of 100 μm and a purity of 99.6% (by area) with no bromine detected. A 20 wt % methanolic solution of the crystals had an APHA color number of 10 or smaller.

Comparative Example 2

Crystallization of TBA was carried out in the same manner as in Example 9, except for replacing the 14 wt % aqueous sodium sulfite solution with water. That is, no reducing agent was introduced. The redox potential during crystallization was about 750 mV (vs. SCE). The TBA slurry concentration after crystallization was 11.7 wt %, and the TBA recovery by crystallization was 99.7 wt %. The resulting dry TBA crystals were considerably yellow-colored crystals having a purity of 99.6% (by area). The bromine content was as high as 16 ppm. A 20 wt % methanolic solution of the crystals had an APHA color number of 290, which supported the appreciable coloration.

Comparative Example 3

To the same equipment as used in Example 9 were continuously and simultaneously fed 600 g/hr of the bromine-containing methanolic TBA solution and 3.8 g/hr of a 32 wt % aqueous hydrazine solution (corresponding to 1.05 equivalent to bromine) while keeping the liquid temperature at 30° C. In this stage, crystallization did not take place, and excess bromine carried over from the preceding bromination reaction was completely reduced to hydrogen bromide.

The resulting methanolic TBA solution and water were continuously and simultaneously fed to the same crystallizer as used in Example 1 at a rate of 603 g/hr and 417 g/hr, respectively, and the resulting TBA slurry having a concentration of 12.6 wt % was continuously discharged from the outlet and worked up to obtain dry TBA crystals. The TBA recovery by crystallization was 99.6 wt %. The dry crystals were white and had a purity of 99.6% (by area) with no bromine detected. A 20 wt % methanolic solution of the resulting crystals had an APHA color number of 10 or smaller. However, involving two separate steps of reduction and crystallization, this method requires equipment for each step, and the operation is complicated.

Comparative Example 4

Into the same equipment as used in Example 9 were put 600 g of the bromine-containing methanolic TBA solution, and 360 g/hr of water and 69 g/hr of 14 wt % aqueous sodium sulfite solution were continuously and simultaneously fed thereto for 1 hour while keeping the liquid temperature at 30° C. with stirring. In about 10 minutes from the start of feeding, TBA began to crystallize. One hour later 1028 g of a TBA slurry having a concentration of 11.7 wt % (crystallization ratio: 99.6 wt %) was obtained. The slurry was separated into a wet cake and a filtrate, and the wet cake was washed with an aqueous methanol solution and dried to give dry TBA crystals, which assumed pale yellow and had a purity of 99.5% (by area) with a bromine content of 5 ppm (by weight). A 20 wt % methanolic solution of the crystals had an APHA color number of 180.

The present invention provides an efficient, effective and economical method of obtaining TBA crystals from a methanolic TBA solution. The effects produced by the present invention are as follows.

(a) The crystallization is in a continuous mode so that the process is simple and efficient.
(b) Where reduction of bromine and crystallization of TBA are carried out simultaneously, TBA crystals are obtained through a single stage.
(c) Where crystallization is carried out through two divided stages, there are obtained high quality single TBA crystals which are as large as 100 to 400 μm and easy to handle.
(d) Having high quality, the TBA crystals obtained through the two-stage crystallization exhibit a lowered APHA color number in an alkaline solution and a reduced hydrolyzable bromine content, as is required of a flame retardant for synthetic resins.
(e) The method involving reduction of bromine can be effected with commonly employed inexpensive reducing agents, which is economically advantageous. The method of the invention does not include co-production of methyl bromide, which is environmentally friendly.

While the invention has been described in detail and with reference to specific embodiments thereof, it will be apparent to one skilled in the art that various changes and modifications can be made therein without departing from the spirit and scope thereof.

What is claimed is:

1. A method of crystallizing tetrabromobisphenol A which comprises continuously and simultaneously feeding a methanolic tetrabromobisphenol A solution and water separately to a first crystallizer to obtain a slurry in which a part of the tetrabromobisphenol A is crystallized and continuously and simultaneously feeding said slurry and water separately to a second crystallizer to crystallize substantially the whole amount of the tetrabromophisphenol A.

2. The method according to claim 1, wherein said methanolic tetrabromobisphenol A solution is a solution obtained by brominating bisphenol A with bromine in a methanolic solvent and treating the reaction mixture with a reducing agent.

3. The method according to claim 2, wherein said reducing agent is hydrazine.

4. The method according to claim 1, wherein the crystallization ratio of tetrabromobisphenol A in said first crystallizer is controlled between 70 and 95% by weight.

5. The method according to claim 1, wherein the total crystallization ratio of tetrabromobisphenol A reached in said second crystallizer is controlled between 97.0 to 99.9% by weight.

6. The method according to claim 1, wherein the crystals of tetrabromobisphenol A obtained in said first and said second crystallizers are single crystals.

7. A method of crystallizing tetrabromobisphenol A which comprises continuously and simultaneously feeding a methanolic tetrabromobisphenol A solution containing bromine, a reducing agent, and water separately to a crystallizer to cause the tetrabromobisphenol A to crystallize and to cause bromine to be reduced simultaneously.

8. The method according to claim 7, wherein said methanolic tetrabromobisphenol A solution containing bromine is a solution obtained by brominating bisphenol A with bromine in a methanolic solvent.

9. The method according to claim 7, wherein said reducing agent is at least one compound selected from the group consisting of hydrazine, sodium sulfite, sodium hydrosulfite, sodium dithionite, and sulfurous acid gas.

10. The method according to claim 7, wherein said reducing agent is fed in an amount of reducing equivalent or more to said bromine in said methanolic tetrabromobisphenol A solution.

11. The method according to claim 7, wherein crystallization of tetrabromobisphenol A is carried out at an oxidation-reduction potential of 600 mV or less with reference to a saturated calomel electrode.

12. A method of crystallizing tetrabromobisphenol A which comprises continuously and simultaneously feeding a methanolic tetrabromobisphenol A solution containing bromine, a reducing agent, and water separately to a first crystallizer to obtain a slurry in which a part of the tetrabromobisphenol A is crystallized and continuously and simultaneously feeding said slurry and water separately to a second crystallizer to crystallize substantially the whole amount of the tetrabromobisphenol A.

13. The method according to claim 12, wherein said methanolic tetrabromobisphenol A solution containing bromine is a solution obtained by brominating bisphenol A with bromine in a methanolic solvent.

14. The method according to claim 12, wherein said reducing agent is at least one compound selected from the group consisting of hydrazine, sodium sulfite, sodium hydrosulfite, sodium dithionite, and sulfurous acid gas.

15. The method according to claim 12, wherein said reducing agent is fed in an amount of reducing equivalent or more to said bromine in said methanolic tetrabromobisphenol A solution.

16. The method according to claim 12, wherein crystallization of tetrabromobisphenol A is carried out at an oxidation-reduction potential of 600 mV or less with reference to a saturated calomel electrode.

17. The method according to claim 12, wherein the crystallization ratio of tetrabromobisphenol A in said first crystallizer is controlled between 70 and 95% by weight.

18. The method according to claim 12, wherein the total crystallization ratio of tetrabromobisphenol A reached in said second crystallizer is controlled between 97.0 to 99.9% by weight.

19. The method according to claim 12, wherein the crystals of tetrabromobisphenol A obtained in said first and said second crystallizers are single crystals.

* * * * *